US00PP27590P3

(12) United States Plant Patent
Dobres

(10) Patent No.: US PP27,590 P3
(45) Date of Patent: Jan. 24, 2017

(54) *CLETHRA* PLANT NAMED 'NOVACLEEIN'

(50) Latin Name: *Clethra alnifolia*
Varietal Denomination: Novacleein

(71) Applicant: CP DELAWARE, INC., Wilmington, DE (US)

(72) Inventor: Michael S. Dobres, Philadelphia, PA (US)

(73) Assignee: CP DELAWARE, INC., Wilmington, DE (US)

( * ) Notice: Subject to any disclaimer, the term of this patent is extended or adjusted under 35 U.S.C. 154(b) by 101 days.

(21) Appl. No.: 14/544,190

(22) Filed: Dec. 9, 2014

(65) Prior Publication Data

US 2016/0165776 P1 Jun. 9, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Buchanan Ingersoll & Rooney PC

(57) ABSTRACT

The new plant resulted from the open pollination of the 'Hummingbird' variety of *Clethra alnifolia* (non-patented in the United States) followed by detailed study and selection from among the progeny. An attractive dense mounding substantially round growth habit is displayed that commonly is taller than that of the 'Hummingbird' variety. Fragrant white flowers commonly are formed during late July through September in longer racemes than the 'Hummingbird' variety. The racemes of the new plant commonly often are twisted and curled. The new plant commonly displays good tolerance to heat, draught, insects and disease. The new plant is well suited for providing attractive ornamentation in a wide range of landscape settings.

2 Drawing Sheets

Botanical classification: *Clethra alnifolia.*
Varietal denomination: cv. Novacleein.

SUMMARY OF THE INVENTION

*Clethra alnifolia* is an ornamental native shrub commonly known as Summersweet or Sweet Pepperbush.

The new plant of the present invention was created through the open pollination of *Clethra alnifolia* 'Hummingbird' (non-patented in the United States) that is maintained at Loxley, Ala., U.S.A. The seed of the 'Hummingbird' variety that was used to produce the new plant of the present invention was collected during the fall of 2007 in Hockessin, Del., U.S.A. The seeds resulting from open pollination were sown during October 2007 at West Grove, Pa., U.S.A. The resulting plants produced by such open pollination were studied in detail during the spring and summer of 2008 and 2009 at West Grove, Pa., U.S.A., for the possible presence of a novel attractive phenotype. A single plant of the present invention was selected and was preserved in view of its unique combination of attractive phenotypic characteristics. Had this plant not been created, identified and preserved it would have been lost to mankind.

It was found that the new *Clethra* plant of the present invention displays the following combination of characteristics:

(a) exhibits an attractive dense mounding substantially rounded growth habit that at maturity commonly is taller than that of the 'Hummingbird' variety,
(b) forms fragrant white flowers in longer racemes than the 'Hummingbird' variety that are often twisted and curled, (c) commonly displays good tolerance to heat, drought, insects and disease, and
(d) is well suited for providing attractive ornamentation in a wide range of landscape settings.

During observations to date, the plant has been found to be hardy to U.S.D.A. Hardiness Zone No. 6.

The new cultivar well meets the needs of the horticultural industry and can be grown to advantage as a perennial garden plant to provide distinctive ornamentation. For instance, it can be grown in parks, gardens and residential settings.

Plants of the new cultivar in view of its combination ion of phenotypic characteristics can be readily distinguished from other *Clethra alnifolia* plants known to its originator. For instance, when compared the 'Hummingbird' variety the new variety commonly forms a taller rounded growth habit and longer racemes. The new variety lacks the more upright growth habit of the 'September Beauty' variety (U.S. Plant Pat. No. 10,481), the pink flowers of the 'Ruby Spice' variety (non-patented in the United States), the lower compact growth habit of the 'Sotite' variety (U.S. Plant Pat. No. 15,505), and the more upright growth habit of the 'Caleb' variety (U.S. Plant Pat. No. 21,589).

The rooting of cuttings has been used to asexually propagate the new variety of the present invention at West Grove, Pa., U.S.A. It has been found that the characteristics of the new cultivar are stable and are reliably transmitted from one generation to another. Accordingly, the new variety can be asexually reproduced in a true-to-type manner.

The new cultivar of the present invention has been named 'Novacleein'.

BRIEF DESCRIPTION OF THE PHOTOGRAPHS

The accompanying photographs illustrate the new cultivar in color as nearly true as it is reasonably possible make the same in color illustrations of this nature. The plants were approximately two years of age and were being grown outdoors in the ground during August 2013 on their own roots at West Grove, Pa., U.S.A.

DETAILED BOTANICAL DESCRIPTION

Figure 1:
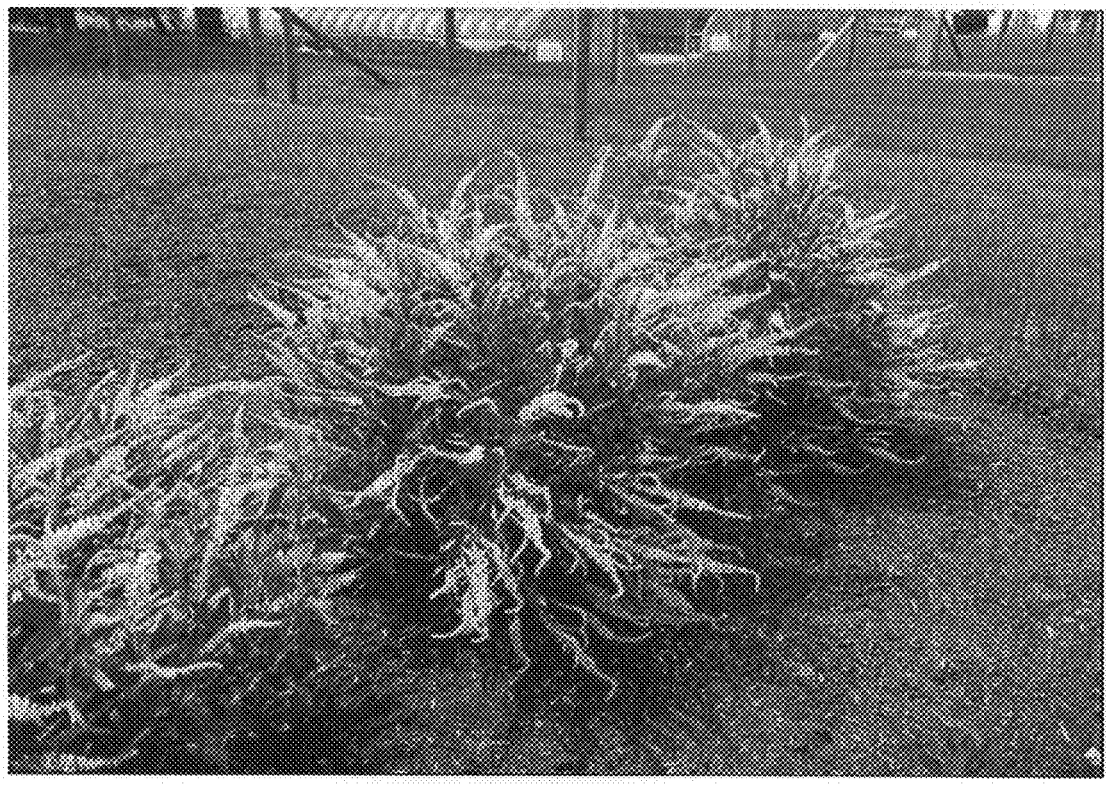
FIG. 1 illustrates specimens of typical mature flowering plants of the new variety. The typical attractive mounding substantially rounded growth habit is shown.
Figure 2:
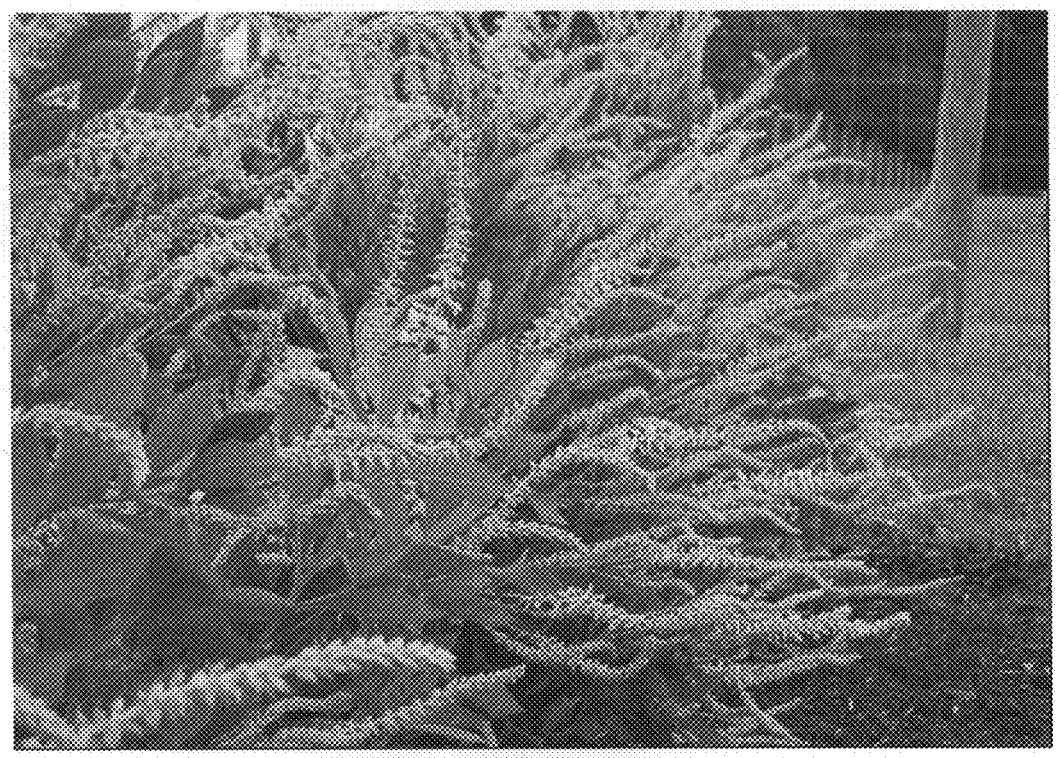
FIG. 2 illustrates a closer view of plants displaying the long often twisted and curled racemes bearing white flowers.

The following is a detailed description while observing three-year-old plants of the new variety that were produced by the rooting of cuttings. Such plants were being grown outdoors in the ground at West Grove, Pa., U.S.A. The chart used in the identification of color is The R.H.S. Colour Chart (1995 Edition) of The Royal Horticultural Society, London, England.

Botanical classification: *Clethra alnifolia*, 'Novacleein' variety.

*Parentage*.—Formed through the open pollination of *Clethra alnifolia*, 'Hummingbird' variety.

*Plant type*.—Deciduous perennial shrub.

Plant:

*Development*.—Initiation of roots from cuttings: commonly approximately 27 days on average; Initiation of young rooted plants from cuttings: commonly approximately 89 days on average.

*Growth habit*.—Mounding and substantially rounded.

*Height*.—Approximately 4 feet on average when mature. This compares to approximately 3 feet when mature for the 'Hummingbird' variety at the same location.

*Spread*.—Approximately 4 feet on average when mature. This compares to approximately 3 feet when mature for the 'Hummingbird' variety at the same location.

*Stem shape*.—Substantially rounded.

*Stem size*.—Length: commonly approximately 76.2 cm on average; Diameter: commonly approximately 0.6-0.7 cm on average.

*Stem texture*.—Somewhat rough.

*Stem color*.—On young wood commonly near Yellow-Green Group 148B, and on old wood near Grey-Brown Group 199A.

*Branching habit*.—Dense and freely-branching.

*Branch angle*.—Branches commonly emerge at an angle of approximately 45 degrees.

*Roots*.—Fibrous network.

Foliage:

*Arrangement*.—Alternate.

*Shape*.—Ovate.

*Apex*.—Apiculate.

*Base*.—Cuneate.

*Length*.—Commonly approximately 9.5 cm on average.

*Width*.—Commonly approximately 3.5 cm on average.

*Attachment*.—Simple.

*Texture*.—On upper surface somewhat rough, and on the under surface substantially smooth.

*Leaf color*.—Spring/Summer: On the upper surface glossy and near Green Group 137A, and on the lower surface near Yellow-Green Group 148B.

*Margins*.—Serrate.

*Venation*.—Pinnate and near Greyed-Green Group 195B in coloration.

*Leaf fragrance*.—None noticeable.

*Petiole size*.—Length: commonly approximately 0.8 cm on average; Diameter: commonly approximately 1.5 mm on average.

*Petiole color*.—Near Green Group 144C.

Inflorescence:

*Flowering season*.—Commonly late July through September at the indicated location.

*Type*.—Positioned separately on racemes.

*Buds*.—Ovoid, approximately 4 mm in length just before opening, approximately 2 mm in diameter, and near White Group 155A in coloration.

*Quantity*.—Very free-flowering, commonly with approximately 133 flowers on average per raceme with approximately 300 racemes being present on a three-year-old plant.

*Raceme length*.—Commonly approximately 12 inches on average. This compares to a length of approximately 6 inches for the 'Hummingbird' variety at the same growing location.

*Raceme diameter*.—Commonly approximately 2.5 cm on average.

*Lastingness*.—Commonly approximately five days on average and influenced by the environmental conditions that are encountered.

*Flower aspect*.—Commonly approximately 90 degrees.

*Flower diameter*.—Approximately 4 mm on average.

*Flower depth*.—Approximately 7 mm on average.

*Petal number*.—Five.

*Petal length*.—Approximately 5 mm on average.

*Petal width*.—Approximately 2 mm on average.

*Petal apex*.—Rounded.

*Petal margin*.—Entire.

*Petal texture*.—Glabrous.

*Petal color*.—Commonly near White Group 155D on the upper surface, and near White Group 155C on the lower surface, both when the flower is opening and when fully opened.

*Sepal number*.—Four.

*Sepal shape*.—Lanceolate.

*Sepal length*.—Approximately 1.5 mm on average.

*Sepal diameter*.—Approximately 3 mm on average.

*Sepal apex*.—Acute.

*Sepal base*.—Fused.

*Sepal margin*.—Entire.

*Sepal texture*.—Glabrous.

*Sepal color*.—Commonly near Green-White Group 157B on the upper surface and near Green-White Group 157A on the under surface.

*Stamen number*.—Ten.

*Anther shape*.—Bi-lobed.

*Anther size*.—Approximately 1 mm in diameter on average.

*Anther color*.—Near Greyed-Orange Group 163D.

*Filament length*.—Approximately 6 mm on average.

*Filament width*.—Commonly less than 1 mm.

*Filament color*.—Near White Group 155A.

*Pollen*.—Commonly present in a moderate quantity, and near Greyed-Orange Group 163D in coloration.

*Pistil number*.—One.

*Stigma shape*.—Tri-lobed.

*Stigma length*.—Approximately 5 mm on average.

*Stigma width*.—Commonly less than 1 mm.
*Stigma color*.—Near White Group 155A.
*Ovary color*.—Near Green Group 138B.
*Ovary shape*.—Generally spherical.
*Ovary length*.—Approximately 1 mm on average.
*Ovary width*.—Approximately 1 mm on average.
*Seeds*.—No seeds are available for observation.
*Fragrance*.—Flowers are sweetly fragrant.
*Peduncle length*.—Commonly approximately 1.5 cm on average.
*Peduncle width*.—Commonly approximately 3 mm on average.
*Peduncle texture*.—Bear short pubescence.
*Peduncle color*.—Commonly near Yellow-Green Group 144A.
*Pedicel length*.—Commonly approximately 5 mm.
*Pedicel width*.—Commonly approximately 1 mm.
*Pedicel texture*.—Bear short pubescence.
*Pedicel color*.—Near Green Group 138D.

Disease resistance: Believed to be typical to that of the species with good tolerance during observations to date.

Plants of the 'Novacleein' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Clethra alnifolia* plant having the following combination of characteristics:

(a) exhibits an attractive dense mounding substantially rounded growth habit that at maturity commonly taller than that of the 'Hummingbird' variety,
(b) forms fragrant white flowers in longer racemes than the 'Hummingbird' variety that are often twisted and curled,
(c) commonly displays good tolerance to heat, drought, insects and disease, and
(d) is well suited for providing attractive ornamentation in a wide range of landscape settings;

substantially as illustrated and described.

* * * * *